United States Patent
Hood et al.

(10) Patent No.: US 7,178,231 B2
(45) Date of Patent: *Feb. 20, 2007

(54) ELECTRODE ASSEMBLY FOR A THERMOKERATOPLASTY SYSTEM USED TO CORRECT VISION ACUITY

(75) Inventors: Larry Hood, Laguna Hills, CA (US); Saeed Steve Khalaj, Laguna Hills, CA (US); Gregg W. Hughes, San Juan Capistrano, CA (US); Paul R. Goth, Mission Viejo, CA (US); Antonio Mendez, Mexicali (MX)

(73) Assignee: Refractec, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/807,646

(22) Filed: Mar. 23, 2004

(65) Prior Publication Data

US 2004/0181218 A1    Sep. 16, 2004

Related U.S. Application Data

(63) Continuation of application No. 10/104,940, filed on Mar. 22, 2002, now Pat. No. 6,723,093.

(51) Int. Cl.
*H01R 13/629*  (2006.01)
*A61F 9/07*  (2006.01)

(52) U.S. Cl. .............................. 29/842; 29/876; 606/5; 606/41

(58) Field of Classification Search ............... 606/4–5, 606/41; 128/898; 29/842–845, 876–877
See application file for complete search history.

(56) References Cited

U.S. PATENT DOCUMENTS

| | | | | |
|---|---|---|---|---|
| 3,552,503 | A * | 1/1971 | Lebar | 175/40 |
| 5,634,921 | A * | 6/1997 | Hood et al. | 606/5 |
| 5,662,647 | A * | 9/1997 | Crow et al. | 606/41 |
| 6,090,107 | A * | 7/2000 | Borgmeier et al. | 606/41 |
| 6,213,997 | B1 * | 4/2001 | Hood et al. | 606/5 |
| 6,299,584 | B1 * | 10/2001 | Iseberg | 600/559 |
| 6,723,093 | B2 * | 4/2004 | Goth et al. | 606/41 |
| 2005/0090816 | A1 * | 4/2005 | McClurken et al. | 606/41 |

* cited by examiner

*Primary Examiner*—Henry M Johnson, III
(74) *Attorney, Agent, or Firm*—Ben J. Yorks; Irell & Manella LLP

(57) ABSTRACT

An electrode assembly that can be used to apply current to a cornea. The assembly includes a tip that is attached to a stop. The stop is pressed into an inner channel of an electrode body. The stop limits the penetration depth of the tip into a cornea.

4 Claims, 3 Drawing Sheets

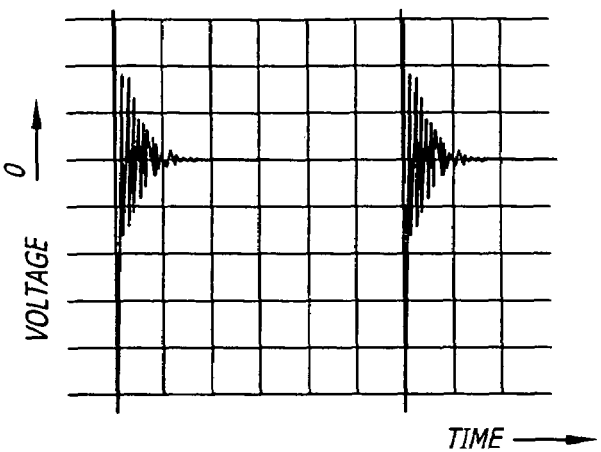
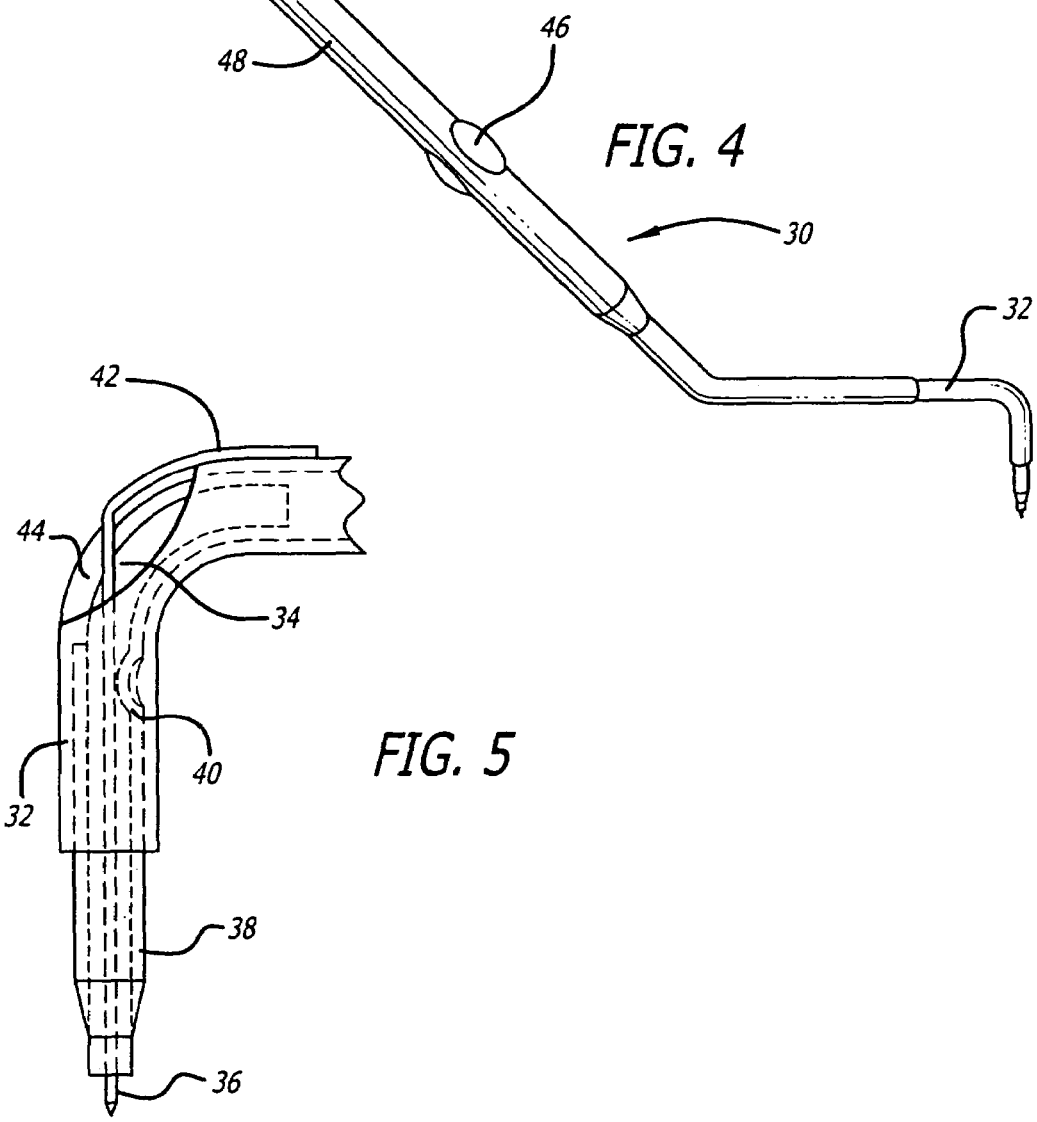

ELECTRODE ASSEMBLY FOR A THERMOKERATOPLASTY SYSTEM USED TO CORRECT VISION ACUITY

CROSS-REFERENCE TO RELATED APPLICATION

The present application is a continuation of U.S. application Ser. No. 10/104,940, filed on Mar. 22, 2002, now U.S. Pat. No. 6,723,093.

BACKGROUND OF THE INVENTION

1. Field of the Invention

The present invention relates to a thermokeratoplasty probe that is placed in direct contact with the outer surface of the cornea.

2. Prior Art

Techniques for correcting vision have included reshaping the cornea of the eye. For example, myopic conditions can be corrected by cutting a number of small incisions in the corneal membrane. The incisions allow the corneal membrane to relax and increase the radius of the cornea. The incisions are typically created with either a laser or a precision knife. The procedure for creating incisions to correct myopic defects is commonly referred to as radial keratotomy and is well known in the art.

Present radial keratotomy techniques generally make incisions that penetrate approximately 95% of the cornea. Penetrating the cornea to such a depth increases the risk of puncturing the Descemets membrane and the endothelium layer, and creating permanent damage to the eye. Additionally, light entering the cornea at the incision sight is refracted by the incision scar and produces a glaring effect in the visual field. The glare effect of the scar produces impaired night vision for the patient.

The techniques of radial keratotomy are only effective in correcting myopia. Radial keratotomy cannot be used to correct an eye condition such as hyperopia. Additionally, keratotomy has limited use in reducing or correcting an astigmatism. The cornea of a patient with hyperopia is relatively flat (large spherical radius). A flat cornea creates a lens system which does not correctly focus the viewed image onto the retina of the eye. Hyperopia can be corrected by reshaping the eye to decrease the spherical radius of the cornea. It has been found that hyperopia can be corrected by heating and denaturing local regions of the cornea. The denatured tissue contracts and changes the shape of the cornea and corrects the optical characteristics of the eye. The procedure of heating the corneal membrane to correct a patient's vision is commonly referred to as thermokeratoplasty.

U.S. Pat. No. 4,461,294 issued to Baron; U.S. Pat. No. 4,976,709 issued to Sand and PCT Publication WO 90/12618, all disclose thermokeratoplasty techniques which utilize a laser to heat the cornea. The energy of the laser generates localized heat within the corneal stroma through photonic absorption. The heated areas of the stroma then shrink to change the shape of the eye.

Although effective in reshaping the eye, the laser based systems of the Baron, Sand and PCT references are relatively expensive to produce, have a non-uniform thermal conduction profile, are not self limiting, are susceptible to providing too much heat to the eye, may induce astigmatism and produce excessive adjacent tissue damage, and require long term stabilization of the eye. Expensive laser systems increase the cost of the procedure and are economically impractical to gain widespread market acceptance and use.

Additionally, laser thermokeratoplastic techniques non-uniformly shrink the stroma without shrinking the Bowmans layer. Shrinking the stroma without a corresponding shrinkage of the Bowmans layer, creates a mechanical strain in the cornea. The mechanical strain may produce an undesirable reshaping of the cornea and probable regression of the visual acuity correction as the corneal lesion heals. Laser techniques may also perforate Bowmans layer and leave a leucoma within the visual field of the eye.

U.S. Pat. Nos. 4,326,529 and 4,381,007 issued to Doss et al, disclose electrodes that are used to heat large areas of the cornea to correct for myopia. The electrode is located within a housing that spaces the tip of the electrode from the surface of the eye. An isotropic saline solution is irrigated through the electrode and aspirated through a channel formed between the outer surface of the electrode and the inner surface of the sleeve. The saline solution provides an electrically conductive medium between the electrode and the corneal membrane. The current from the electrode heats the outer layers of the cornea. Heating the outer eye tissue causes the cornea to shrink into a new radial shape. The saline solution also functions as a coolant which cools the outer epithelium layer.

The saline solution of the Doss device spreads the current of the electrode over a relatively large area of the cornea. Consequently, thermokeratoplasty techniques using the Doss device are limited to reshaped corneas with relatively large and undesirable denatured areas within the visual axis of the eye. The electrode device of the Doss system is also relatively complex and cumbersome to use.

"A Technique for the Selective Heating of Corneal Stroma" Doss et al., Contact & Intraoccular Lens Medical Jrl., Vol. 6, No. 1, pp: 13–17, January–March, 1980, discusses a procedure wherein the circulating saline electrode (CSE) of the Doss patent was used to heat a pig cornea. The electrode provided 30 volts r.m.s. of power for 4 seconds. The results showed that the stroma was heated to 70° C. and the Bowman's membrane was heated 45° C., a temperature below the 50–55° C. required to shrink the cornea without regression.

"The Need For Prompt Prospective Investigation" McDonnell, Refractive & Corneal Surgery, Vol. 5, January/February, 1989 discusses the merits of corneal reshaping by thermokeratoplasty techniques. The article discusses a procedure wherein a stromal collagen was heated by radio frequency waves to correct for a keratoconus condition. As the article reports, the patient had an initial profound flattening of the eye followed by significant regression within weeks of the procedure.

"Regression of Effect Following Radial Thermokeratoplasty in Humans" Feldman et al., Refractive and Corneal Surgery, Vol. 5, September/October, 1989, discusses another thermokeratoplasty technique for correcting hyperopia. Feldman inserted a probe into four different locations of the cornea. The probe was heated to 600° C. and was inserted into the cornea for 0.3 seconds. Like the procedure discussed in the McDonnell article, the Feldman technique initially reduced hyperopia, but the patients had a significant regression within 9 months of the procedure.

Refractec, Inc. of Irvine Calif., the assignee of the present application, has developed a technique to correct hyperopia with a thermokeratoplasty probe that is in direct contact with the cornea. The probe includes a tip that is inserted down into the stroma layer of a cornea. Electrical current flows through the eye to denature the collagen tissue within the stroma. The process of inserting the probe tip and applying electrical current can be repeated throughout the cornea. The denatured tissue will change the refractive characteristics of the eye.

FIG. 11 shows an electrode 1 of a handpiece (not shown) used to apply current to a cornea. The electrode 1 includes a wire tip 2 that is crimped onto an electrode body 3. To minimize scarring in the cornea the wire tip 2 is very small, on the order of 0.1 millimeters. Crimping such a small tip can be very difficult, particularly when attempting to mass produce the electrode 1.

The electrode 1 also includes a stop 4 that limits the insertion depth of the tip 2. It is critical that the tip 2 not be inserted past the stroma layer of the cornea into the endothelial layer or inner ocular chamber. Over insertion of the tip may cause permanent damage to the eye. It has been found that the stop 4 may become dislodged and slide along the length of the wire tip 2. When this occurs the stop 4 will no longer limit the insertion depth of the tip 4.

BRIEF SUMMARY OF THE INVENTION

An electrode assembly that can be used to apply current to a cornea. The assembly includes a tip that is attached to a stop. The stop extends into an inner channel of an electrode body.

BRIEF DESCRIPTION OF THE DRAWINGS

FIG. 3 is a graph showing a waveform that is provided to the probe of the system;

FIG. 4 is a side view of an electrode assembly for a handpiece of the system;

FIG. 5 is an enlarged cross-sectional view of a tip of the electrode assembly;

DETAILED DESCRIPTION

Figure 2:
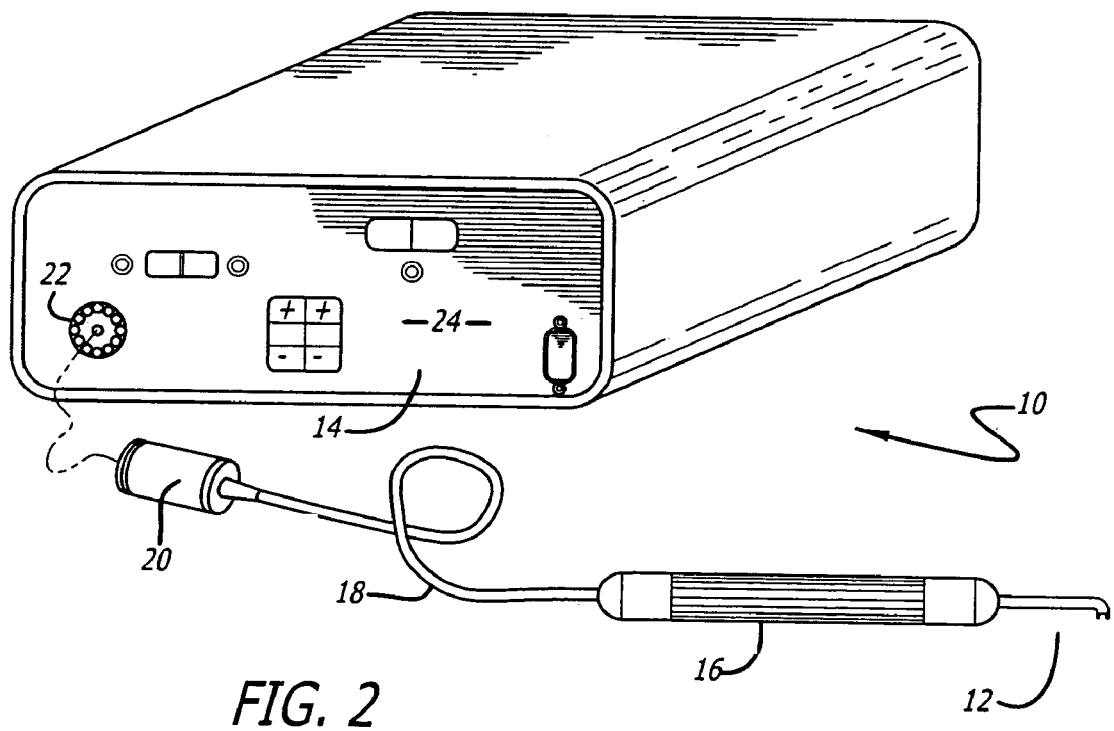
FIG. 2 is a perspective view of a thermokeratoplasty electrode system.

Referring to the drawings more particularly by reference numbers, FIG. 2 shows a thermokeratoplasty electrode system 10 of the present invention. The system 10 includes an electrode probe 12 coupled to a power supply unit 14. The power supply unit 14 contains a power supply that can deliver electrical power to the probe 12. The probe 12 has a hand piece 16 and wires 18 that couple the probe electrode to a connector 20 that plugs into a mating receptacle 22 located on the front panel 24 of the power supply 14. The hand piece 16 may be constructed from a non-conductive material.

The system 10 also includes a ground element (not shown) that is in contact with the patient to provide a return path for the electrical current provided by the power supply to the probe 12. By way of example, the ground element may be a lid speculum that is used to maintain the patient's eyelids in an open position.

The power supply 14 provides a predetermined amount of energy, through a controlled application of power for a predetermined time duration. The power supply 14 may have manual controls that allow the user to select treatment parameters such as the power and time duration. The power supply 14 can also be constructed to provide an automated operation. The supply 14 may have monitors and feedback systems for measuring tissue impedance, tissue temperature and other parameters, and adjust the output power of the supply to accomplish the desired results. The unit may also have a display that indicates the number of remaining uses available for the probe 12.

In one embodiment, the power supply provides a constant current source and voltage limiting to prevent arcing. To protect the patient from overvoltage or overpower, the power unit 14 may have an upper voltage limit and/or upper power limit which terminates power to the probe when the output voltage or power of the unit exceeds a predetermined value.

The power unit 14 may also contain monitor and alarm circuits which monitor the resistance or impedance of the load and provide an alarm when the resistance/impedance value exceeds and/or falls below predefined limits. The alarm may provide either an audio and/or visual indication to the user that the resistance/impedance value has exceeded the outer predefined limits. Additionally, the unit may contain a ground fault indicator, and/or a tissue temperature monitor. The front panel of the power unit typically contains meters and displays that provide an indication of the power, frequency, etc., of the power delivered to the probe.

The power unit 14 may deliver a power output in a frequency range of 5 KHz–50 MHz. In the preferred embodiment, power is provided to the probe at a frequency in the range of 500 KHz. The unit 14 is designed so that the power supplied to the probe 12 does not exceed 1.2 watts (W). The time duration of each application of power to a particular corneal location is typically between 0.1–1.0 seconds. The unit 14 is preferably set to deliver approximately 0.75 W of power for 0.75 seconds.

FIG. 3 shows a typical voltage waveform that is applied by the unit 14. Each pulse of energy delivered by the unit 14 is a highly damped signal, typically having a crest factor (peak voltage/RMS voltage) greater than 10:1. Each power dissipation is provided at a repetitive rate. The repetitive rate may range between 4–12 KHz and is preferably set at 8 KHz.

The system may have a switch which controls the application of power to the probe 12. The power unit 14 may also contain a timer circuit which allows power to be supplied to the probe 12 for a precise predetermined time interval. The timer may be a Dose timer or other similar conventional circuitry which terminates power to the probe after a predetermined time interval. The unit may also allow the user to apply power until the switch is released. As one embodiment, the power supply may be a unit sold by Birtcher Medical Co. under the trademark HYFRECATOR PLUS, Model 7-797 which is modified to have voltage, waveform, time durations and power limits to comply with the above cited specifications.

FIGS. 4 and 5 show an electrode assembly 30 that can be used to apply current to a cornea. The electrode assembly 30 is plugged into the handpiece 16 shown in FIG. 2. The electrode assembly 30 includes a body 32 that has an inner channel 34. The body 32 is constructed from an electrically conductive material. By way of example, the body 32 may be constructed from a stainless steel.

The assembly 30 includes a tip 36 that is attached to a stop 38. The stop 38 limits the insertion depth of the tip 36 into a cornea. The tip 36 is constructed from an electrically conductive material. By way of example, the tip 36 may be constructed from a stainless steel wire. The stop 38 is preferably constructed from a dielectric material such as synthetic resinous fluorine-containing polymers, commonly sold as TEFLON, a registered trademark of E.I. DuPont Nemour.

The stop 38 is pressed into the inner channel 34 of the body 32. The body 32 preferably contains a mechanical stop 40 that limits the depth at which the tip stop 38 can be pressed into the inner channel 34. The mechanical stop 40 may be a dimple formed into the body 32.

A proximal end 42 of the wire tip 36 can be spot welded to the electrode body 32 to electrically connect the body 32 to the tip 36. The wire tip 36 may extend through an opening 44 so that the tip 36 can be routed through the inner channel 34 and welded to the outside surface of the body 32.

The electrode body 32 may also have a pair of flanges 46 on a shank portion 48 of the body 32. The shank portion 48 is inserted into the handpiece 16 of the probe 12 shown in FIG. 2. The flanges 46 prevent rotation of the electrode body 32 and wire tip 36 within the handpiece 16. It is important that the tip 36 not move during a procedure.

The electrode assembly 30 can be assembled by first attaching the stop 38 to the wire tip 36. This can be done with an adhesive or other attachment means. The tip stop 38 is then pressed into the inner channel 34 of the body 32 until the end of the stop 38 engages the mechanical stop 40. Attaching the tip 36 to the stop 38 and then pressing the stop 38 into the body 32 simplifies the assembly process. Simplifying the assembly reduces the cost of producing the electrode 30. Pressing the stop 38 into the body 32 also increases the structural integrity of the electrode 30 and reduces the likelihood that the stop 38 will slide along the tip 36.

Figure 1:
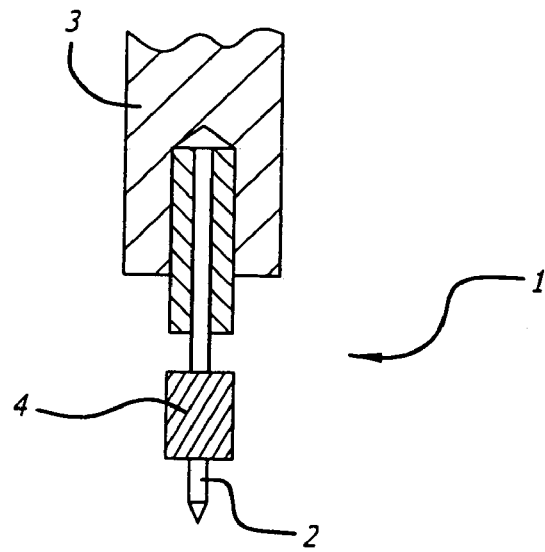
FIG. 1 is a side view of an electrode tip assembly of the prior art.

The proximal end 42 of the wire tip 36 is routed through the opening 44 and spot welded to the body 32. Spot welding will produce higher part yields than the crimping process described relative to the prior art electrode shown in FIG. 1.

The electrode assembly 30 is then inserted into the handpiece 16 shown in FIG. 2 to complete the assembly.

Figure 6:
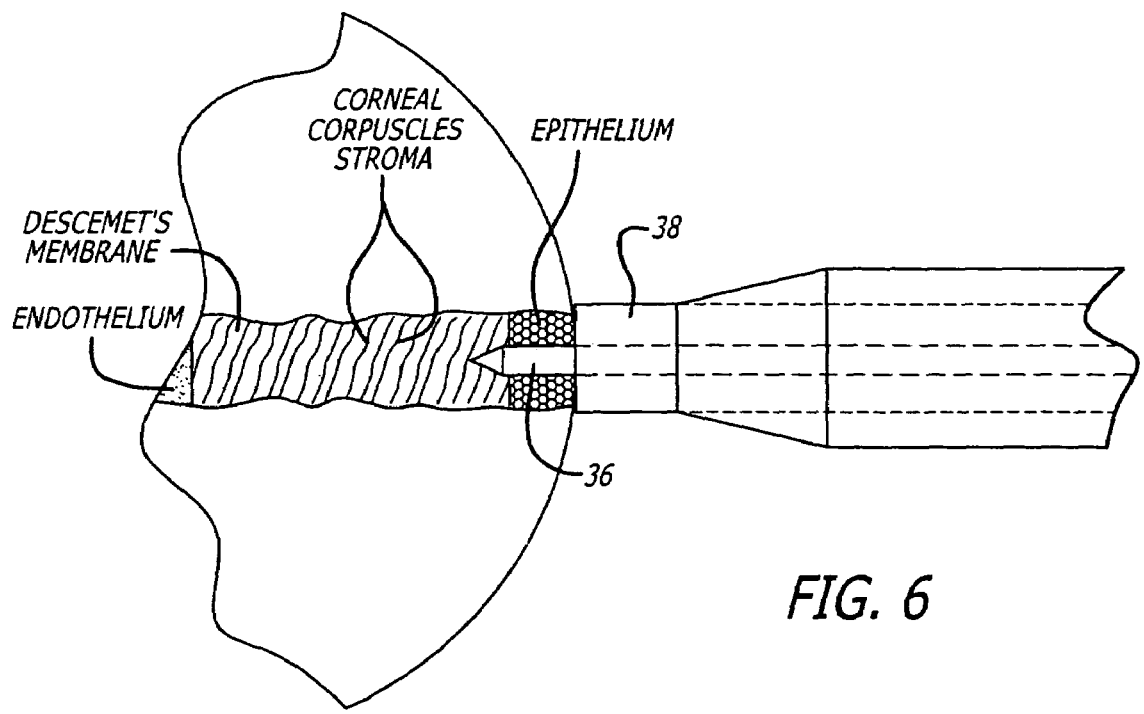
FIG. 6 is an enlarged view of the probe tip inserted into a cornea.
Figure 7:
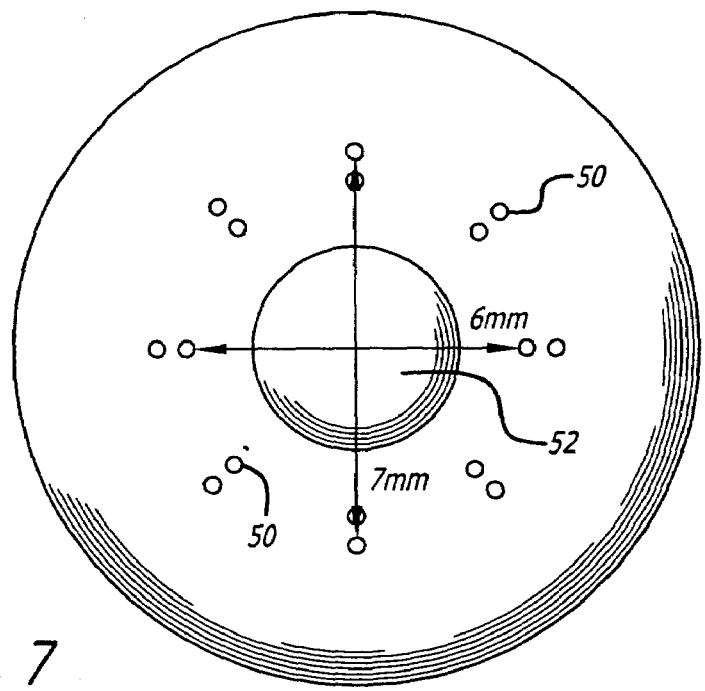
FIG. 7 is a top view showing a pattern of denatured areas of the cornea.

As shown in FIG. 6, during a procedure, the tip 36 is inserted into a cornea. The length of the tip 36 is typically 300–600 microns, preferably 400 microns, so that the electrode enters the stroma. The stop 38 limits the penetration of the tip 36. The diameter of the tip 36 is preferably 125 microns. The tip diameter is small to minimize the invasion of the eye.

The power supply provides a current to the cornea through the tip 36. The current denatures the stroma to correct the shape of the cornea. Because the tip 36 is inserted into the stroma it has been found that a power no greater than 1.2 watts for a time duration no greater than 1.0 seconds will adequately denature the corneal tissue to provide optical correction of the eye. The frequency of the power is typically between 1–20 KHz and preferably 4 KHz. Inserting the tip 36 into the cornea provides improved repeatability over probes placed into contact with the surface of the cornea, by reducing the variances in the electrical characteristics of the epithelium and the outer surface of the cornea.

FIG. 6 shows a pattern of denatured areas 50 that have been found to correct hyperopic conditions. A circle of 8 or 16 denatured areas 50 are created about the center of the cornea, outside the visual axis portion 52 of the eye. The visual axis has a nominal diameter of approximately 5 millimeters. It has been found that 16 denatured areas provide the most corneal shrinkage and less post-op astigmatism effects from the procedure. The circle of denatured areas typically have a diameter between 6–8 mm, with a preferred diameter of approximately 7 mm. If the first circle does not correct the eye deficiency, the same pattern may be repeated, or another pattern of 8 denatured areas may be created within a circle having a diameter of approximately 6.0–6.5 mm either in line or overlapping.

The exact diameter of the pattern may vary from patient to patient, it being understood that the denatured spots should preferably be formed in the non-visionary portion 52 of the eye. Although a circular pattern is shown, it is to be understood that the denatured areas may be located in any location and in any pattern. In addition to correcting for hyperopia, the present invention may be used to correct astigmatic conditions. For correcting astigmatic conditions, the denatured areas are typically created at the end of the astigmatic flat axis. The present invention may also be used to correct radial keratotomy procedures that have overcorrected for a myopic condition.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for assembling an electrode assembly that is used to apply a current to a cornea, comprising:
    attaching a stop to a tip, the tip extends from the stop such that the stop limits an insertion depth of the tip into the cornea;
    pressing the stop into an inner channel of a body;
    welding the tip to the body; and,
    inserting the body into a handpiece.

2. The method of claim 1, wherein the stop is inserted into the inner channel of the body until the stop engages a mechanical stop of the body.

3. A method for assembling an electrode assembly that is used to apply a current to a cornea, comprising:
    bonding a stop to a tip, the tip extends from the stop such that the stop limits an insertion depth of the tip into the cornea;
    pressing the stop into an inner channel of a body; and,
    inserting the body into a handpiece.

4. The method of claim 3, wherein the stop is inserted into the inner channel of the body until the stop engages a mechanical stop of the body.

* * * * *